United States Patent [19]
Smith, Jr. et al.

[11] 4,361,401
[45] Nov. 30, 1982

[54] AUTOMATIC SAMPLE DEPOSITION IN FLAMELESS ANALYSIS

[75] Inventors: Stanley B. Smith, Jr., Westford; Robert G. Schleicher, Bradford; Edward C. Eldred, Wenham, all of Mass.

[73] Assignee: Instrumentation Laboratory Inc., Lexington, Mass.

[21] Appl. No.: 161,879

[22] Filed: Jun. 23, 1980

Related U.S. Application Data

[63] Continuation of Ser. No. 907,973, May 22, 1978, abandoned.

[51] Int. Cl.³ .................. G01N 1/10; G01N 21/74
[52] U.S. Cl. ...................................... 356/36; 356/312
[58] Field of Search .................. 356/36, 312, 315, 317

[56] References Cited
U.S. PATENT DOCUMENTS

| | | | |
|---|---|---|---|
| 3,525,476 | 8/1970 | Boling et al. | 239/338 |
| 3,788,752 | 1/1974 | Salvin et al. | 356/36 |
| 3,806,250 | 4/1974 | George | 356/315 |
| 3,819,279 | 6/1974 | Braun et al. | 356/312 |
| 3,866,831 | 2/1975 | Denton | 356/315 X |
| 3,893,769 | 7/1975 | Woolley | 356/312 |
| 4,009,963 | 3/1977 | George | 356/312 |
| 4,022,530 | 5/1977 | Braun et al. | 356/312 |
| 4,042,303 | 8/1977 | Huber | 356/312 |
| 4,201,469 | 5/1980 | Matousek et al. | 356/312 X |

OTHER PUBLICATIONS

Matousek, "Aerosol Deposition in Furnace Atomization", Talanta, vol. 24, No. 5, May 1977, pp. 315-319.
Manufacturers Brochure on Perkin-Elmer Models 290B and 303, Atomic Absorption Spectrophotometers.

Primary Examiner—F. L. Evans

[57] ABSTRACT

Method and apparatus for automatically depositing predetermined reproducible amounts of nebulized samples into a furnace atomizer of an atomic absorption spectrophotometer, the atomizer being provided with an aperture, wherein a plurality of sample containers containing samples to be analyzed are arranged and successively transported on a sample supporting device, with the sample containers being open at their upper ends. The samples are aspirated from the containers via a suitable means and into a nebulizer-mixing chamber device wherein they are nebulized and mixed until such time that the nebulized sample achieves full equilibrium therein. A means is provided for depositing the nebulized and now equilibrated sample from the chamber device through the aperture into the furnace atomizer. The deposition of predetermined and reproducible amounts of nebulized samples is controlled by a means which, in a preferred embodiment, comprises a vacuum source in valved communication with the means for depositing the nebulized sample in a way that aerosol deposition is effected only during the time period when the vacuum source is shut off from the means for depositing the aerosol sample by shutting off the valve.

In another preferred embodiment, the means for controlling the amount of aerosol sample being deposited comprises a fluidic switch in communication with the nebulizer-mixing chamber device on the one hand and with the means for depositing the sample on the other. Hence, sample deposition takes place only during the time period when such communication from the chamber device to the deposition means is effected by the fluidic switch.

17 Claims, 11 Drawing Figures

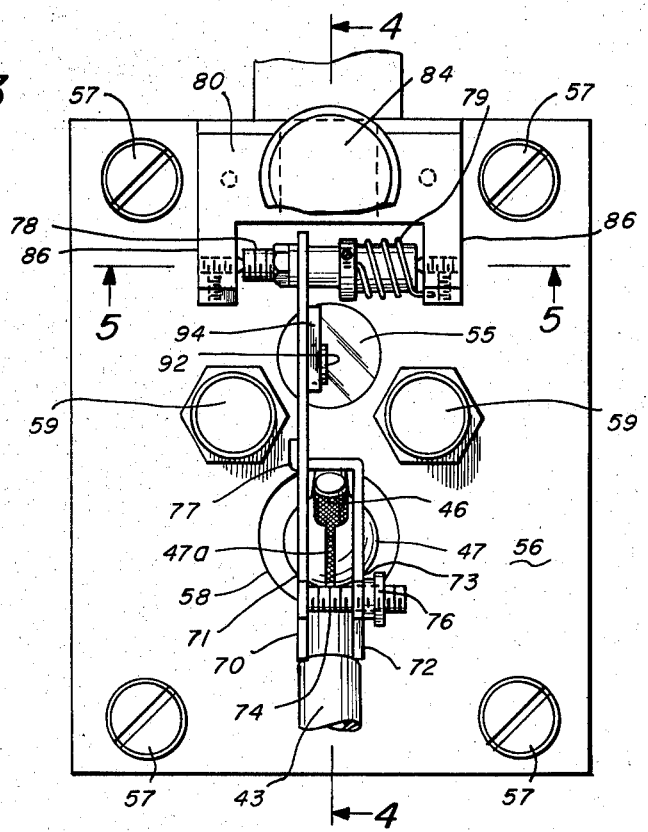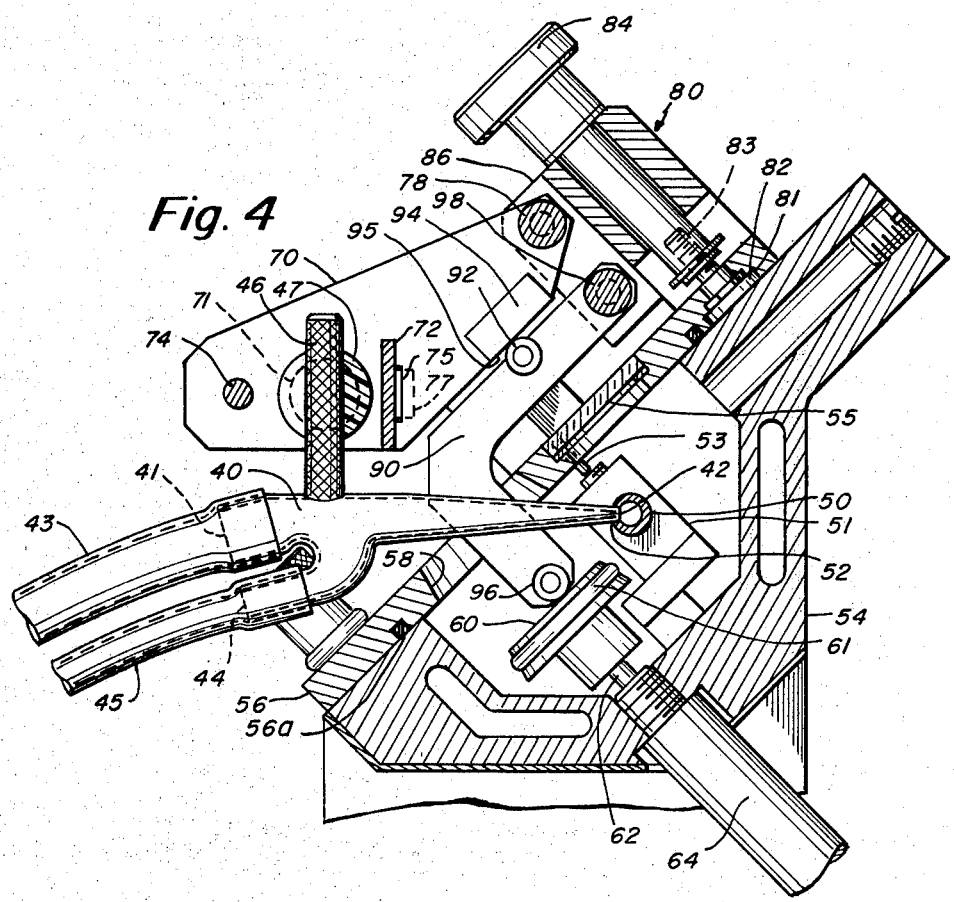

ESTABLISHING EQUILIBRIUM

DEPOSITION

PURGE + READY TO INTRODUCE NEW SAMPLE

AUTOMATIC SAMPLE DEPOSITION IN FLAMELESS ANALYSIS

This is a continuation of application Ser. No. 907,973 filed May 22, 1978, now abandoned.

BACKGROUND OF THE INVENTION

This invention relates to a method and apparatus for automatically depositing predetermined and reproducible amounts of nebulized samples to be analyzed through an aperture into a furnace atomizer of a flameless atomic absorption spectrophotometer.

In flameless atomic absorption, the atomic cloud of the sample whose absorption is to be measured is generated in a furnace atomizer which normally is made of graphite formed into the shape of a cylindrical tube and provided with a radial aperture at about the midpoint between its ends, with this radial port serving as the introduction aperture through which a sample may be introduced therein. The furnace atomizer, i.e., the cylindrical graphite sample tube, is designed to be heated by having an electrical current passed therethrough through electrodes in contact with its respective ends, all as is well known in the art. The cylindrical configuration of the furnace atomizer permits a beam of radiation of selected spectral characteristics to be directed through the atomic cloud generated therein to effect analysis thereof in a manner well known in the art of atomic absorption spectroscopy. Normally atomization, i.e., the generation of the atomic cloud from the sample deposited therein, is performed in three stages, namely a first stage of drying the sample, a second stage of ashing the sample, and finally a third stage of atomizing the sample, e.g., the generation of the atomic cloud of the sample. Since the last stage of atomization requires the application of extremely high temperatures, the furnace atomizer is normally enveloped in a mantle of a protective inert gas, which may be Argon or Nitrogen, to prevent its combustion, although it is made of graphite. In addition, cooling means may be provided for the electrodes surrounding the ends of the furnace atomizer and also in the walls of the housing containing the furnace atomizer, all as is well known in the art.

Furnace atomizers exhibit very high analytical sensitivity when compared to conventional flame analyzers. In fact, in some applications, furnace atomizers are so sensitive as to require large dilutions combined with very small quantities of samples. Normal sample quantities deposited into furnace atomizers range between five (5 $\mu$l) to fifty (50 $\mu$l) microliters and are generally introduced by means of a hand held micropipette through the aperture into the furnace atomizer. Such a manual loading entails grave, however, disadvantages in that it requires not only the continuous presence of an operator, but more importantly it relies on the skill and dexterity of the operator in depositing predetermined and hence reproducible amounts of such small quantities into the furnace atomizer, a requirement that is difficult for anyone to achieve and to continue achieving, especially when carrying out a series of atomic absorption measurements over an extended period of time. The reproducibility of the sample amounts deposited is crucial to achieving reproducible results, since it is well known in the art that the intensity of the signal realized in flameless atomic absorption measurements is directly proportional to the amount of sample that has been deposited in the furnace atomizer.

Accordingly, it is a principal object of the present invention to provide a method and apparatus that automatically deposits predetermined and reproducible amounts of very small quantities of nebulized samples into a furnace atomizer of a flameless atomic absorption spectrophotometer that will produce reproducible results. A further objection of the present invention resides in the provision of a method and apparatus of the above-mentioned type in which cross-contamination between successive samples has been reduced to a level of insignificance. Still another object of the present invention resides in the provision of a method and apparatus of the above-mentioned type in which deposition is effected only after the nebulized sample has achieved complete equilibrium in the nebulizer-mixing chamber device of the apparatus of the invention.

PRIOR ART

The closest prior art known to applicants is the one disclosed by J. P. Matousek in an article entitled, "Aerosol Deposition in Furnace Atomization," that was published in the Journal of *Talanta*, Volume 24, No. 5, May 1977, pages 315 to 319, issued and printed by the Pergamon Press, Great Britain. In the Matousek system there is disclosed a nebulizer-spray chamber combination with a droplet separator and delivery tube to deposit aerosol samples into a furnace atomizer of a flameless atomic absorption spectrophotometer. As stated on page 316, column 1, line 5 et seq., "The quantity of analyte accumulated in the furnace is accurately controlled by timing the aerosol production by means of the solenoid valve. Alternatively, measured volumes of the analyte solution can be nebulized." Thus, Matousek attempts to control the amounts deposited in the furnace atomizer by controlling the amounts his system produces at the nebulizer end. He achieves this either by controlling the duration of the nebulization process by a solenoid, as he states, by providing to the nebulizer only a precisely-measured volume of the analyte solution which can be nebulized. Since he controls only at the source of production, there are still small but significant changes in the amount of sample being deposited which adversely affect reproducibility of results. This is due not only because of the physical distance separating the source of aerosol sample production from the point of aerosol sample deposition but, more significantly, because of slight changes in nebulization efficiency occurring especially during the turn-on and the turn-off portions of the aerosol sample generation cycle. A further disadvantage resides in that when the nebulizer in the Matousek disclosure is turned off, a small amount of sample remains in the nebulizer tubing which contributes to cross-contamination between successive samples and thus again adversely affects reproducibility of results.

An apparatus having a graphite tube furnace for flameless atomic absorption spectroscopy is disclosed in U.S. Pat. No. 4,022,530, including having a sample port and electrodes and for passing an electrical current through the tube, with the electrodes being surrounded by cooling jackets; an apparatus to which applicants' invention may be readily adapted. U.S. Pat. No. 4,042,303 teaches an automated method and apparatus for introducing very small quantities of samples, of the order of up to about 20 microliters, into a graphite tube of an atomic absorption spectrophotometer. This patent also recognized that manual pipetting of such small samples required not only the continuous presence of an operator but also a disproportionately large amount of time when carrying out a series of atomic absorption measurements. This patent effects sample deposition, not aerosol deposition, by means of an introduction device employing sample containers open at both ends whereby samples contained therein are introduced into the furnace by pressure applied at the upper end of the container when the bottom end thereof is thrust into the aperture of the graphite furnace.

U.S. Pat. No. 3,893,769 discloses a graphite tube furnace in which as gas inlet tube is mounted tangentially so as to impart a swirling motion to the flow of inert gas enveloping the graphite tube furnace. U.S. Pat. No. 3,819,279 discloses an atomization device in which the graphite tube is surrounded by at least one radiation absorbing protective jacket so as to reduce thereby the amount of electric energy necessary to heat the graphite tube to a particular temperature. U.S. Pat. No. 4,009,963 discloses an arrangement for producing free atoms in which the furnace is surrounded by cooling means so as to obviate some of the disadvantages occasioned by high teperatures, namely the reaction of water vapor with graphite dust, a combination that adversely affects the stability of the measuring signal. U.S. Pat. No. 3,788,752 discloses a controller to control the flow of the inert purging gas to the heated graphite tube so that during the atomization stage of the heating cycle, the atomized sample is not readily swept out of the graphite tube.

U.S. Pat. No. 3,806,250 discloses a nebulizer assembly for use in flame spectroscopy comprising a nebulizing nozzle, a cloud chamber and, more specifically an impact surface in the form of a spherical bead located in front of the nebulizing nozzle which is adjustable during operation. The position of this impact surface in front of the nebulizing nozzle improves its performance by breaking up the larger droplets and decreasing the proportion of the smaller droplets, enabling thus the concentration of sample atoms in the analytical flame to be increased, thus increasing the overall sensitivity of the device. U.S. Pat. No. 3,525,476 discloses a pneumatic nebulizer in which in lieu of the impact surface previously mentioned, a secondary stream of fuel and air is supplied in a counter stream designed to impinge on the primary sample stream so as to further reduce the size of nebulized samples, with the patent being assigned to the same assignee of the present invention.

Finally, U.S. Pat. No. 3,866,831 discloses a method and apparatus for nebulizing relatively small liquid samples for use in flame spectroscopic analysis in which a transducer is energized for a preselected pulse or nebulization time to achieve an optimum aerosol density thereby, i.e., it controls the production of aerosol samples by controlling the nebulization time: A teaching that is similar to that disclosed in the Matousek article first above mentioned.

SUMMARY OF THE INVENTION

In general, the invention provides a method and apparatus useful and adaptable as an accessory to any flameless atomic absorption spectrophotometer, so as to make it into a truly automated one by enabling the spectrophotometer to perform, entirely unattended by an operator, flameless spectrophotometric analyses of a multiplicity of samples. The only task the operator needs to do is to turn on the respective switches, set the appropriate controls, position a plurality of samples contained in suitable sample containers on a sample transport arrangement and then flip some toggle switches to their desired positions in order to set the entire analysis process of all of the samples into motion. Depending upon the particular spectrophotometer used, such analysis may include as many as ninety-five samples in which each sample may be analyzed for at least two constituent elements, thus making for a total of 190 sample determinations with up to ten replicates per sample determination entirely automatically. Again, depending upon the particular spectrophotometer employed, a printer may be provided which presents a written record of each of these 1900 determinations at the conclusion of the analysis process.

More specifically, the apparatus for the automatic deposition of predetermined reproducible amounts of aerosol samples into a furnace atomizer of an atomic absorption spectrophotometer comprises a sample transport means designed for arranging and successively transporting a plurality of sample containers containing samples to be analyzed, in which the sample containers are open at their upper ends, in a manner so as to present sample containers one by one with respect to an aspirating means such as a pick-up probe designed for vertical displacement between an operative downward position in which the pick-up probe is positioned within a sample container and an up or inoperative position in which the pick-up probe is positioned free of the sample containers so as to permit the movement and indexing of these sample containers in a horizontal plane with respect to the pick-up probe.

Furthermore, there is provided a nebulizer-mixing chamber device having communication, on the one hand with the pick-up probe and with a suitable deposition means at the other. It is to be understood that the deposition means is designed automatically to be positioned in communication with an introduction aperture of the furnace atomizer prior to and during the deposition of the aerosol sample therein. Following such deposition of the aerosol sample, the deposition means is furthermore designed automatically to be disengaged not only from the introduction aperture of the furnace atomizer but also to be withdrawn from the housing hermetically enclosing the furnace atomizer. A control means for controlling the deposition of predetermined and reproducible amounts of aerosol samples from the deposition means into the furnace atomizer is operatively connected to the deposition means about midway between its respective ends and, in one embodiment essentially comprises a vacuum source which is in valved communication with the deposition means so as to assure that aerosol deposition by the deposition means is effected only during the time period when the vacuum source is shut off from the deposition means by shutting off the valve. In another embodiment, the means for controlling the amount of aerosol deposition essentially comprises a fluidic switch which, through one of its two outputs, operatively connects the nebulizer-mixing chamber device with the deposition means so as to assure that aerosol deposition into the furnace atomizer is effected only during the time period when the fluidic switch does effectuate such communication between the nebulizer-mixing chamber device and the deposition means. The second output of the fluidic switch is in communication with the nebulizer-mixing chamber device during all other time periods when aerosol deposition is not to take place. It is to be understood that other means for controlling the amount of aerosol deposition may readily suggest themselves to those skilled in the art which means may be interpositioned between the nebulizer-mixing chamber device and the aerosol deposition means, it being critical only that such means can precisely control the deposition of aerosol samples by effectively preventing deposition except during the predetermined time period when deposition is to take place.

In general, the method for the automatic sample deposition of predetermined reproducible amounts of aerosol samples into a furnace atomizer of an atomic absorption spectrophotometer comprises the steps of arranging and successively transporting a plurality of sample containers containing samples to be analyzed with respect to a pick-up probe, aspirating such samples seriatim from such containers and nebulizing and mixing the aspirated samples in a suitable chamber device until full equilibrium of the aerosol mist generated is achieved therein by successively removing nebulized sample from the chamber device as it is being nebulized, establishing communication between the chamber device and the introduction aperture of the furnace atomizer and, ceasing for a set time interval the removal of nebulized sample from the chamber device while maintaining the communication between the device and the furnace atomizer, permitting thereby the deposition of predetermined reproducible amounts of equilibrated aerosol samples from the chamber device into the furnace atomizer.

BRIEF DESCRIPTION OF THE DRAWINGS

In order that the invention may be clearly understood and readily carried into effect, an embodiment thereof will now be more fully described, by way of example, with reference to the accompanying drawings in which:

FIG. 3 is a plan view in the direction of the arrows and along the line 3—3 of FIG. 2, on a still larger scale, showing the cover plate of the furnace housing and particularly showing the opening through which the deposition means may enter into the housing;

FIG. 4 is a section, partly in elevation and along the line 4—4 of FIG. 3, and specifically showing the deposition means in position within the introduction aperture of the furnace atomizer immediately preceding and during the time period of aerosol deposition therein, also showing the means for supporting and arcuately guiding the deposition means for entry into the furnace housing;

Figure 1:
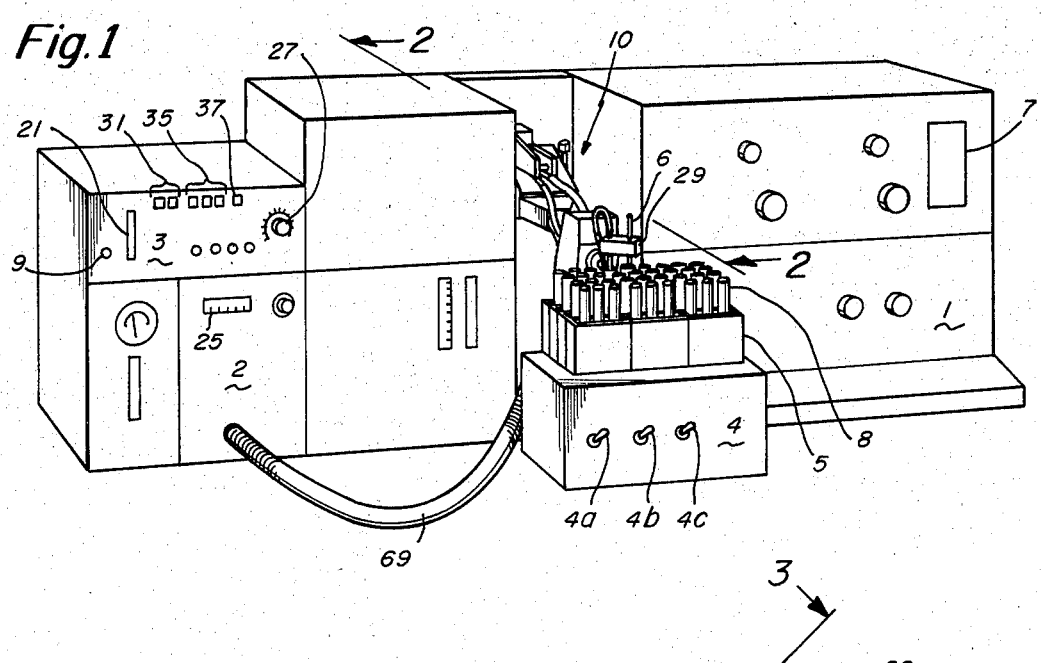
FIG. 1 is a perspective view of a dual-channel double-beam absorption spectrophotometer together with its flameless furnace power and control module to which the apparatus of the invention has been adapted and showing particularly the aerosol sample control module, the sample transport arrangement with sample containers thereon, and the sample deposition module in place and embodying and constructed in accordance with the present invention.

Referring now to the drawings in which like reference numerals refer to like parts throughout and first in particular to FIG. 1, reference numeral 1 designates a dual-channel double-beam atomic absorption spectrophotometer provided with a printer 7 and all the required controls and dials for its operation. It is to be understood, however, that the present invention is equally applicable to other flameless spectrophotometers than the one shown, i.e., to a single-channel single-beam atomic absorption spectrophotometer or the like. The flameless furnace furnace power and control module 2 is shown to the left of the spectrophotometer and is designed to provide all the power, control and gas requirements to the furnace atomizer, and may incorporate stages of temperature controls and their respective durations and timing, together with gas flow controls, pressure regulators and other switches as may be required for the proper operation of a flameless atomizer, all as is well known to persons skilled in the art. It also shows a furnace atomizer temperature indicator 25 by means of which an operator can readily ascertain the temperature at which the furnace atomizer finds itself at any particular point of its operation, the significance of which will become more apparent from the description of the operation of the invention below. A hose 69 is shown emanating from this flameless furnace power and control module 2 and is designed to connect it to the furnace atomizer. This hose 69 contains all the required wirings and tubes carrying the gases, the power, the signals, the pressures, the cooling liquid, etc. that are needed for the proper operation of the furnace atomizer.

Positioned on top of this flameless furnace power and control module 2 is the aerosol sample control module 3 which forms an operative part of the present invention and is designed to control the functioning of aerosol sample production, its deposition time, any repetitions of sampling as desired, nebulizer gas flow, and including a turning knob 27 which is useful in matching door opening to the desired temperature at which the deposition of aerosol sample is to take place, all as will be more fully explained below when describing the operation of the apparatus of the invention.

Substantially at the center and immediately in front of the spectrophotometer 1 is shown a suitable sample transport arrangement 4 with its three toggle switches 4a, 4b and 4c, on top of which is shown a series of removable racks 5, with each such rack 5 designed to hold five sample containers 8. Of course, it is to be understood that the configuration of such a sample transport arrangement 4 may be as desired and thereby one can vary the maximum number of sample containers 8 that may be accommodated thereon, all as well known to persons skilled in the art. In the preferred embodiment shown in FIG. 1, there are customarily nineteen such removable racks 5, with each rack 5 containing five sample containers 8, making for a total of ninety-five such sample containers, with each container having about 12 ml. capacity. A lifter rod 6 having a horizontal arm 29 mounted thereon is designed removably to accommodate therein a suitable pick-up probe and to have two positions for such probe, an "up" or inoperative position, and a "down" or operative position, as will be more fully described below. The sample deposition module 10 is mounted just behind the sample transport arrangement 4 and is designed to connect it operatively to the flameless furnace atomizer.

Figure 2:
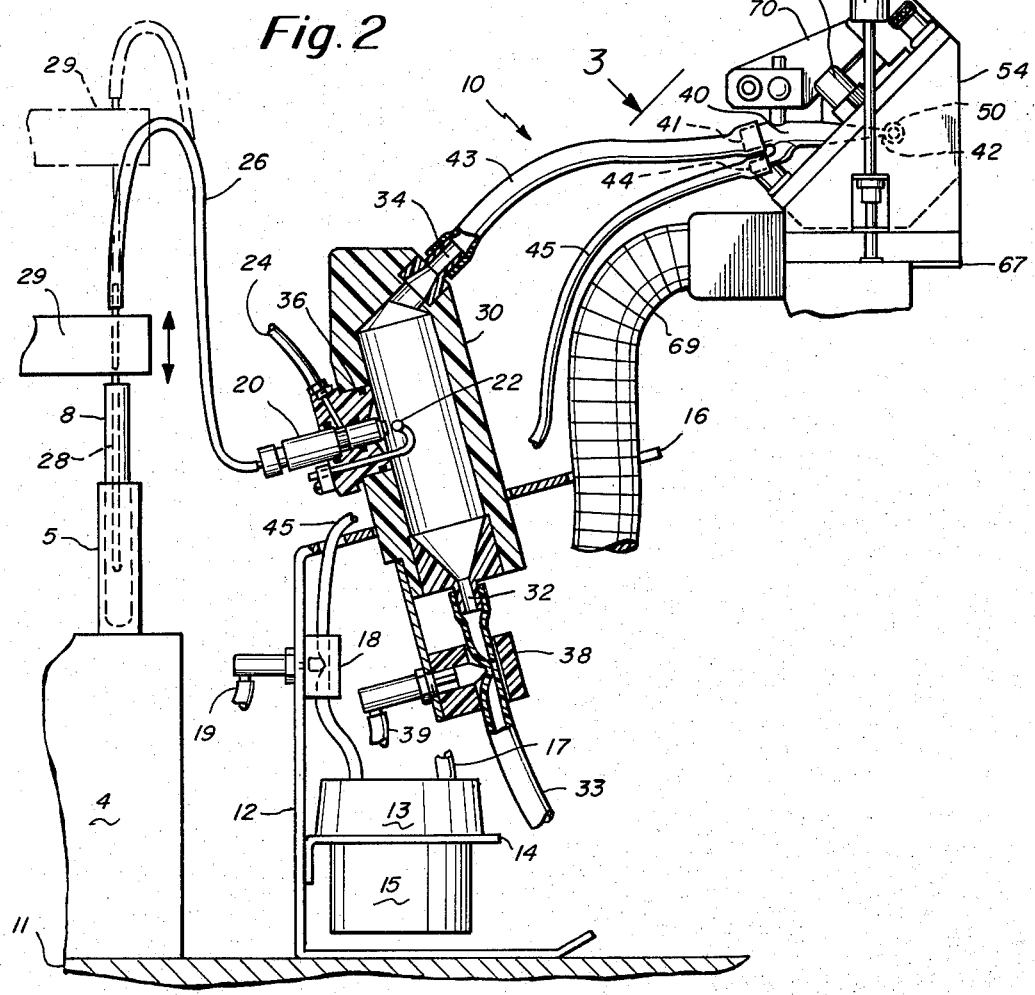
FIG. 2 is a section, partly in elevation, on an enlarged scale, along the line 2—2 of FIG. 1, particularly depicting the sample deposition module in operative communication with the sample transport arrangement on the one hand and with the furnace atomizer at the other.

FIG. 2 is an elevational section on an enlarged scale and along the line 2—2 of FIG. 1 showing particularly the sample deposition module 10 and how the same is in operative communication with the sample transport arrangement 4 on the one hand and with the furnace atomizer 50 on the other. The pick-up probe 28, which is shown in its "down" operative position within the sample container 8, is connected by a flexible hose 26 to a nebulizer 20 which is of conventional construction and is being provided with an adjustable impact surface 22. Another flexible hose 24 attached to the nebulizer 20 is designed to carry the nebulizing gas under pressure to it, which gas may be air, all as is well known in the art and as disclosed in some of the patents discussed in the Prior Art Statement hereinabove.

The nebulizer 20 is mounted in one wall of a mixing chamber 30 within a suitable opening 36 formed therein. Essentially, the mixing chamber 30 internally is designed as a vertical cylinder with a funnel-like bottom opening 32 to which is connected a flexible hose 33 going to waste (not shown). A convenient pinch valve arrangement 38 is mounted just below the mixing chamber 30 and may be pneumatically operated through connecting hose 39 to effect pinching off hose 33 when so desired. At the upper end of the mixing chamber 30 there is provided a second opening 34 to which is attached flexible hose 43 connecting at its other end to the deposition means, shown in this embodiment as a jet tube 40. The forward end of jet tube 40 is tapered to form a delivery nozzle 42 shown in communication with the furnace atomizer 50, as will be described in more detail with respect to FIG. 4. Between the end 41 of jet tube 40 on the one hand and the delivery nozzle 42 on the other there is provided a connecting tube 44 which through another flexible hose 45 is connected to a suitable trap 15. A second pinch valve arrangement 18 is also associated with this hose 45 just above the trap 15 so as to permit the pinching off of this tube, and is actuated through a pneumatic hose 19 connected to a pneumatic source, not shown. It is to be understood, however, that these pinch valves 18 and 38 may be operated by other known means, whether they be electric or electronic, all as well known in the art.

For convenience, both the nebulizer 20 and the mixing chamber 30 as well as the two pinch valve arrangements 18 and 38, together with the trap 15, may be conveniently secured to or mounted on a suitable support 12 secured to a base 11, just adjacent the sample transport arrangement 4 which base 11 may be connected to or form a part of the base (not shown) of the spectrophotometer 1. The mixing chamber is mounted within a suitable opening of an inclined plate 16 properly secured to the support 12 and is also provided with openings for the flexible hose 69 and hose 45, substantially as shown. The furnace atomizer 50, which may comprise a graphite tube, is supported within a hermetically sealed furnace housing 54. Leveling means 66 cooperating with a supporting base 67 for the housing 54 may be provided so as to adjust the horizontal position of the furnace atomizer 50 precisely with respect to the beam of light generated in the spectrophotometer so as to insure that it passes substantially through the central axis of the furnace atomizer 50. The trap 15 is shown secured to the support 12 by means of a plate 14 and is furthermore provided with a cover 13 so as to hermetically seal the trap 15. In addition to valved hose 45 entering the trap 15 through this cover 13, a further flexible hose 17 is shown having communication with the trap 15 at its one end, with its other end being connected to a source of vacuum (not shown), preferably having a value between about 200 to about 300 torr, and a capacity of at least seven liter per minute.

FIG. 3 depicts the front cover plate 56 for the furnace housing 54 and is a plan view in the direction of the arrows and along the line 3—3 of FIG. 2, but on a still larger scale. It particularly shows the opening 58 in this cover plate 56 through which the deposition means is designed to enter into the housing so as to make communication with the furnace atomizer 50 therein. The cover plate 56 is removably secured to the housing 54 by suitable mounting screws 57, and an "O" ring 56a, as may be best observed in FIG. 4, insures air-tight communication with the housing. FIG. 4 is an elevational section along the line 4—4 of FIG. 3 and specifically shows the deposition means, herein a jet tube 40, within the introduction aperture 52 of the furnace housing, more specifically the delivery nozzle 42 of the jet tube 40 introduced into the furnace atomizer 50 through an introduction aperture 52 thereof. FIG. 4 also depicts, together with FIG. 3, the means for supporting and arcuately guiding the deposition means, herein the jet tube 40, for entry into the furnace housing 54. This means for supporting and arcuately guiding the jet tube 40 essentially comprises a mounting and pivot block 80 secured to the upper central portion of the cover plate 56 by means of a suitable mounting plate 82 fastened to the cover plate 56 and accommodated within a suitable recess 81 of the cover plate 56. A mounting screw arrangement 83, actuated by securing knob 84, is designed manually and removably to secure the mounting and pivot block 80 to the mounting plate 82 and hence therethrough also to the cover plate 56. Block 80 is furthermore formed with a pair of bearing supports 86 within which is mounted two pivot shafts, namely pivot shaft 78 to secure the swing arm 70 and pivot shaft 98 to secure the "L"-shaped actuating arm 90, all of which together comprise the means for supporting and arcuately guiding the jet tube 40 into operative engagement with the furnace atomizer 50. A torsion spring 79 is wound about shaft 78 and connects under tension swing arm 70 with bearing support 86, the significance of which will become apparent from the description of the operation of the invention. The cover plate 56 is also provided with a window 55, enabling an operator to view the furnace atomizer 50 during its operation. Additionally, the cover plate 56 displays a pair of cylinders 59 designed to accommodate spring-biased prongs 53 which assist in securing the furnace atomizer 50 firmly in position when the cover plate 56 is in place with the prongs 53 shown cooperating with the furnace support 51, substantially as shown in FIG. 4.

The swing arm 70 is designed removably to hold the jet tube 40 which, for this purpose is provided with a mounting rod 46, preferably burred on its outer surface and integrally formed with the jet tube 40. A flexible mounting ball 47, axially split as at 47a, is designed conveniently to be slipped over the burred mounting rod 46 and being accommodated therewith in a hole 71 formed in the swing arm 70 on the one hand and another hole 73 formed in an "L"-shaped ball clamp 72 on the other. The clamp 72 is designed removably to be fastened to swing arm 70 by its lip 77 passing through a slit 75 in the arm 70 on the one hand and by means of a clamp nut 76 and clamp screw 74 at the other.

A small plate 94 secured to the underside of swing arm 70 acts as a race 95 for an upper roller 92 mounted on the "L"-shaped actuating arm 90, as may be best observed in FIG. 4. The actuating arm 90 is also provided with a lower roller 96 designed to contact and run on the surface of a tapered door 60 intended hermetically to enclose, through its sealng "O" ring 61, the previously-mentioned opening 58 formed in the front cover plate 56 of the furnace housing 54. This tapered door 60 may preferably be pneumatically actuated between two of its operative positions, an inner position as shown in FIG. 4 in which the opening 58 is open, and an upper position shown in FIG. 6 in which the opening 58 is hermetically sealed off thereby. Actuation of the door 60 between its two operative positions may conveniently be effected through a pneumatic cylinder 64 and a shaft 62 connecting with the door 60.

Figure 5:
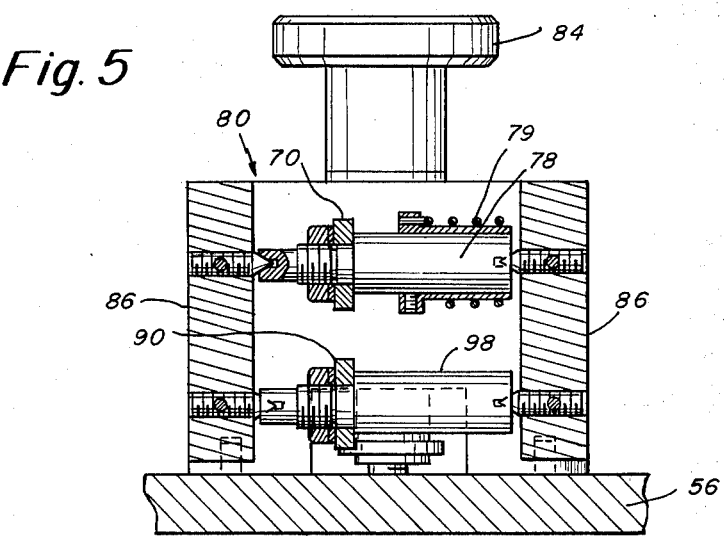
FIG. 5 is a section, partly in elevation, in the direction of the arrows and along the line 5—5 of FIG. 3, of the mounting and pivot block for the supporting and arcuately guiding means of the deposition means which is secured to the front cover plate of the furnace housing.
Figure 6:
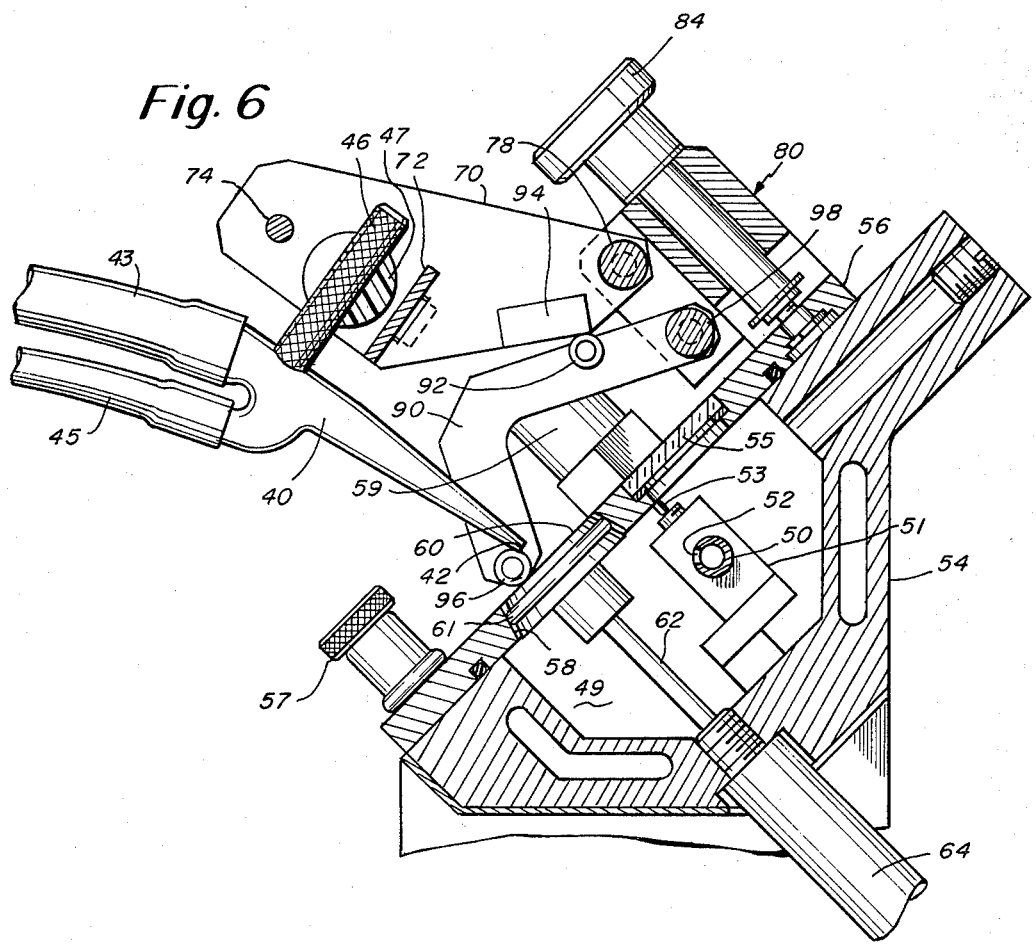
FIG. 6 is a view similar to that shown in FIG. 4, but showing the deposition means withdrawn from both the furnace atomizer and the furnace housing, a position assumed by the deposition means immediately following the deposition of aerosol sample into the furnace atomizer.

FIG. 5 is an elevational section in the direction of the arrows and along the line 5—5 of FIG. 3, and depicts the mounting and pivot block 80, especially showing the anchoring of the pivot shafts 78 and 98 within the bearing supports 86. FIG. 6 on the other hand is a view similar to that shown in FIG. 4, but showing the deposition means in the withdrawn position from both the furnace atomizer 50 and also the furnace housing 54, which is the position assumed by the deposition means immediately following the deposition of an aerosol sample into the furnace atomizer 50. It is to be noted that the deposition means may be locked in the shown withdrawn position as depicted in FIG. 6, if so desired. This can be conveniently accomplished by a suitable plunger and/or a locking arrangement (not shown) as is well known to persons skilled in the art.

Figure 7:
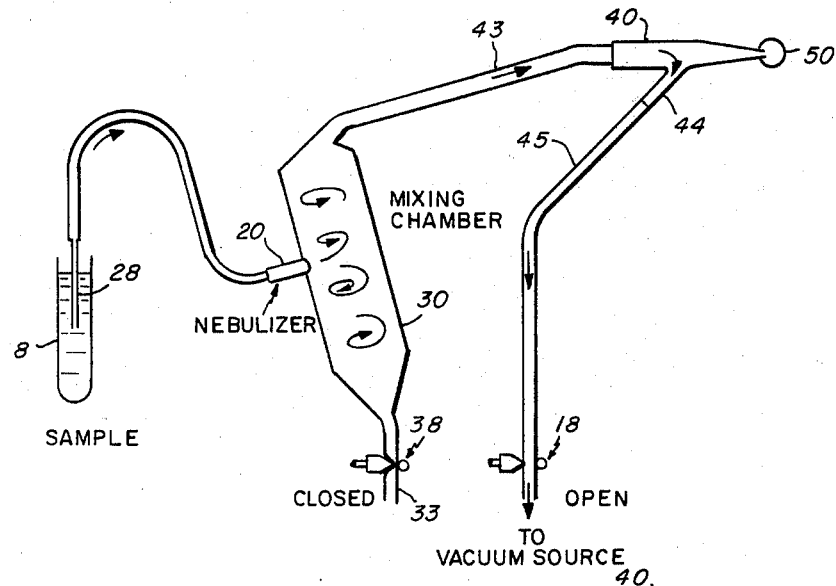
FIGS. 7, 8 and 9 are schematic views of the various positions assumed by the operative parts embodying the present invention and helpful in understanding the steps of the method of the invention in carrying out deposition of predetermined reproducible amounts of equilibrated aerosol samples into a furnace atomizer.
Figure 8:
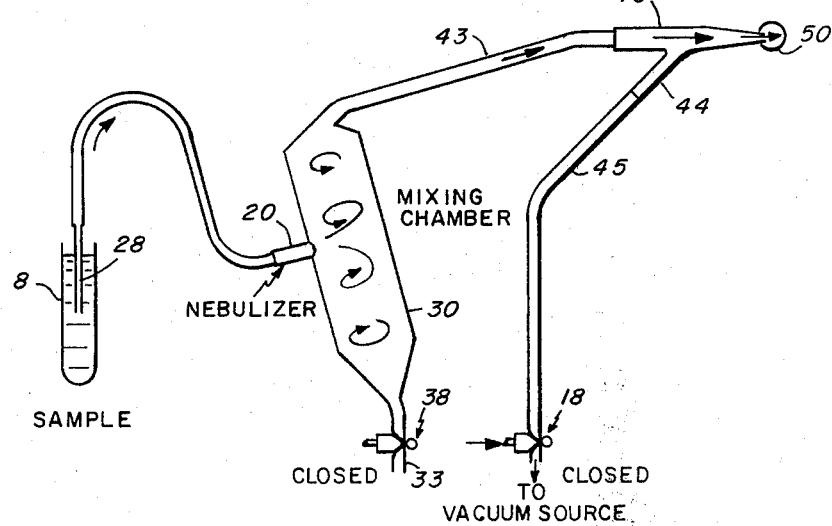
Figure 9:
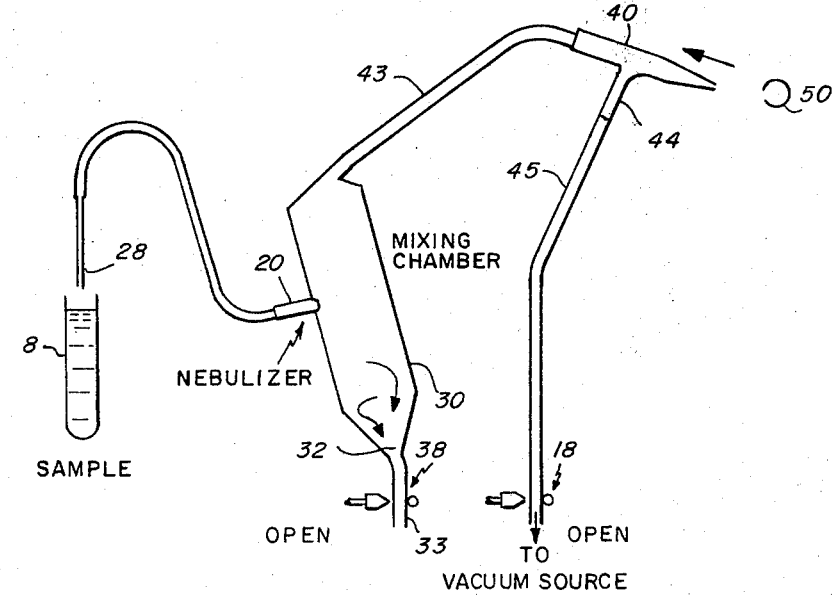

The operation of the preferred embodiment of the invention hereinbefore described may now be more fully explained with reference to the schematic views of the various positions assumed by the operative parts embodying the present invention and as shown in FIGS. 7, 8 and 9. As already mentioned, it is a feature of the present invention to assure that complete equilibrium of the aerosol sample is achieved within the nebulizer-mixing chamber device before any part of the generated aerosol mist is allowed to enter into the furnace atomizer 50 of the atomic absorption spectrophotometer. This step of establishing equilibrium is schematically depicted in FIG. 7 which is, of course, to be considered in view of the other drawings already described.

As may be noted from FIGS. 1, 4 and 7, the operator would have first selected the operative parameters for the particular sample run by turning the respective controls found on the face of both the spectrophotometer 1 and its flameless furnace power and control module 2, all as is well known to persons skilled in the art.

He would thereafter turn on the power switch 9 on the aerosol sample control module 3, noting the nebulizer flow indicator 21 for its proper functioning and, by observing the furnace atomizer temperature indicator 25, select the desired temperature at which deposition is to take place which, of course, means as to when the door 60 of the furnace housing 54 is to open, i.e., to assume the position shown in FIG. 4, so as to permit the entry of the deposition means into the housing 54 and by its delivery nozzle 42 enter the introduction aperture 52 of the furnace atomizer. This he does by matching the desired temperature observed on the indicator 25 by turning knob 27 until the door 60 does open at that desired temperature shown on the indicator 25. The operator may of course select any temperature; applicants consider that by selecting a relatively high temperature, say about 150° C., the sampling speed can be increased by eliminating the first stage of drying and, at the end of the cycle, by reducing the cooldown time of the furnace, since the furnace need not have to be cooled except to this temperature.

Thereafter, the operator manually dials in the time he considers is required to establish complete equilibrium of the aerosol sample within the nebulizer-mixing chamber device, which time is normally expressed in seconds and set in the two windows indicated as at 31. The operator then selects the deposition time, again in seconds, by dialing that time in in the three-window arrangement shown as at 35. As is well understood by those skilled in the art, by lengthening the deposition time, one increases the amount of sample deposited and thus enhances the concentration sensitivity of the instrument. Since it is also well known to those skilled in the art that flameless atomizers as contrasted with flame atomizers exhibit a very high sensitivity, the controls at 35 allow the operator to dial in a low deposition time period, as low as one second. Next, the operator determines as to how often each measurement is to be repeated by the instrument for each sample by manually dialing in that number as at 37. Then by flipping toggle switches 4a, 4b and 4c to their respective operative positions, the operator actuates the sample transport arrangement 4 and sets whether the same is to operate in a manual or automatic mode, all as is well known to persons skilled in the art. Thereupon a sample container 8 containing a sample to be analyzed is positioned by the sample transport arrangement 4 in position with respect to the pick-up probe 28, and by actuating lifter rod 6, the arm 29 carrying the pick-up probe is caused to move downward, positioning thereby the pick-up probe into the sample container 8, as may be best observed in FIGS. 2 and 7. Due to the flow of the nebulizer gas through flexible hose 24 and into the nebulizer 20, sample contained within sample container 8 begins to be aspirated therefrom, nebulized by the nebulizer 20, with the larger droplets being further broken up by striking the adjustable impact surface 22, and the aerosol mist thus generated begins to fill the mixing chamber 30 and gradually the flexible hose 43, and thereby the deposition means, namely the jet tube 40. It is to be noted that during this equilibration period the delivery nozzle 42 of the jet tube 40 has already entered into the furnace atomizer 50 through its introduction aperture 52, as shown in FIG. 4. Since the pinch valve arrangement 38 is closed, no sample mist can escape through the bottom end 32 of the mixing chamber 30. The other pinch valve arrangement 18, however, is in its open position and since a vacuum communication is thus established between trap 15 and the jet tube 40 via the flexible hose 45, any nebulized aerosol sample reaching the jet tube 40 at the point where the connecting tube 44 connects therewith is effectively removed thereby into the trap 15. In fact, due to the strength of the vacuum source, namely being from about 200 to about 300 torr, not only all nebulized aerosol sample reaching the jet tube 40 is removed but in addition, some air or gases that may be present within the furnace atomizer 50 are also removed thereby. As a consequence, during this delay cycle, the entire aerosol sample production system is effectively flushed and stabilized, removing thereby any traces of previous sample leftovers that may have remained therein or in the furnace atomizer 50 and all the tubings, so as to achieve a stabilized system characterized by high reliability and virtually no carryover in between samples, making cross-contamination for all practical purposes insignificant.

Once the temperature has been selected at which the door 60 is to open by the turning of knob 27 as above mentioned, the pneumatic cylinder 64 is actuated to cause the door to open by moving it to the position shown in FIG. 4. Thereupon, the actuating arm 90 with its lower roller 96 riding on the face of the door 60, is designed to move into the furnace housing 54 through the opening 58 by the combined actions of gravity and of torsion spring 79 forcing the swing arm 70 to follow closely the actuating arm 90 and, in fact, exert some pressure thereon through race 95 bearing against at upper roller 92. It is to be noted that the swing arm 70, which removably carries the jet tube 40, goes through a wider arcuate motion than does actuating arm 90. Thus, the delivery nozzle 42 also goes through a wider arc than does the roller 96 on the actuating arm 90. This may be better visualized by comparing FIGS. 4 and 6, where in the latter figure the delivery nozzle 42 is adjacent the bottom roller 96 and yet at the completion of the motion as shown in FIG. 4, the distance traveled by bottom roller 96 is exceeded by the distance traveled by the delivery nozzle 42, which is now in position with the introduction aperture 52 of the furnace atomizer 50. Care therefore must be exercised by the operator in securing the jet tube 40 to the swing arm 70 in such a manner that the delivery nozzle 42 is precisely aligned within the introduction aperture 52 at the conclusion of its arcuate motion into the furnace housing 54.

Having achieved complete equilibrium of the nebulized aerosol sample within the mixing chamber 30 and the hoses 43 and 45 as well as within the jet tube 40, deposition for the preset time period as dialed in the windows as at 35 may now take place. This aerosol deposition is depicted schematically in FIG. 8. Whereas during the time period set for establishing equilibrium, the pinch valve arrangement 18 on hose 45 leading to the trap 15 (and hence to a source of vacuum) is in the open position, connecting thereby the mixing chamber 30 and jet tube 40 to vacuum. During the deposition time period, however, this pinch valve arrangement 18 is actuated so as to pinch off the flexible hose 45. As a consequence, the jet tube 40 and mixing chamber 30 are effectively shut off from the vacuum source while the nebulization-mixing process still continues. The net effect is to propel the aerosol mist from the mixing chamber 30 through the flexible hose 43 and by means of the jet tube 40, more specifically through the delivery nozzle 42 thereof, directly into the furnace atomizer 50.

At the expiration of the preset time period as manually dialed in in the windows at 35, the following events are caused to take place in short succession one after another and as partly shown in the schematic of FIG. 9, depicting "purge and ready to introduce new sample." About simultaneously with the opening of the pinch valve arrangement 18, the pneumatic cylinder 64 is actuated so as to move the door 60 to its position shown in FIG. 6, hermetically sealing off the furnace housing 54. Through the cooperation of rollers 96 and 92 of the actuating arm 90, the swing arm 70 causes the jet tube 40 to be effectively removed from both the furnace atomizer 50 as well as from the inside 49 of housing 54. It should be noted that immediately upon the opening of the pinch valve 18, the deposition means, i.e., the jet tube 40, is once again connected to the source of vacuum so that no further aerosol mist can thereafter travel beyond the point where the tube 44 is connected thereto, namely toward the delivery nozzle 42, but is rather being carried away through hose 45 and into the trap 15.

About the time and shortly after the door 60 effects the hermetical sealing of the furnace housing 54, the furnace atomizer 50 is quickly brought to its second stage, that of ashing the deposited aerosol sample, followed by the third stage of atomization, and then the measurement of the atomized sample, all as is well known to those skilled in the art.

Also substantially about the same time, the flow of nebulizing gas through flexible hose 24 is interrupted and lifter rod 6 actuated to move upward, carrying arm 29 and thereby the pick-up probe 23 with it until the tip thereof fully clears the top of the sample container 8, substantially as shown in FIG. 9. Also, about the same time the second pinch valve arrangement 38 is actuated to the open position, permitting thereby any aerosol mist and condensed sample remaining within the mixing chamber 30 to escape through its bottom end 32 and hose 33 to waste or another source of vacuum (not shown) as may be desired. Due to the continued application of vacuum through hose 45, the entire system is effectively purged of most if not all of the residue of the aerosol sample that was just subjected to analysis, and the system rendered ready for the introduction of a new sample. This may, of course, be achieved automatically by the sample transport arrangement 4 moving one of the removale racks 5 just enough to index another sample container 8 into alignment with the pick-up probe 28 which remains in its upper inoperative position until the indexing is finished, whereupon a new sampling cycle is ready to commence, all as already described.

Figure 10:
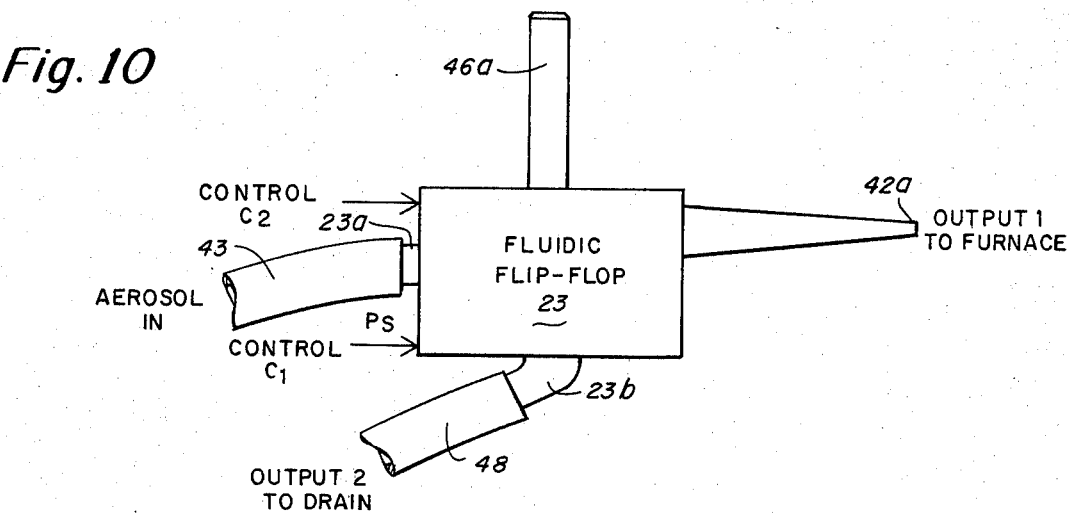
FIG. 10 is a schematic view of another preferred embodiment of a control means that may be employed for controlling the amount of aerosol deposition into a furnace atomizer.

In FIG. 10 is disclosed a second preferred embodiment of a control means that may be employed for controlling the amount of aerosol deposition into a furnace atomizer. Herein the control means comprises a fluidic switch 23 having one input 23a to which flexible hose 43 is connected for admitting aerosol mist therein, and two outputs, namely Output 1 to the furnace atomizer and represented by a delivery nozzle 42a, and Output 2, 23b to which flexible hose 48 is connected leading to drain (not shown) but is not connected to any vacuum source as in the first embodiment. Such fluidic flip-flop switches are, of course, well known in the art and are operated by application of control signals at two control ports, C1 and C2. The fluidic flip-flop 23 is a memory device, i.e., its designated output, whether it be Output 1 or Output 2, will not change its state even after the removal of the control signal.

Figure 11:
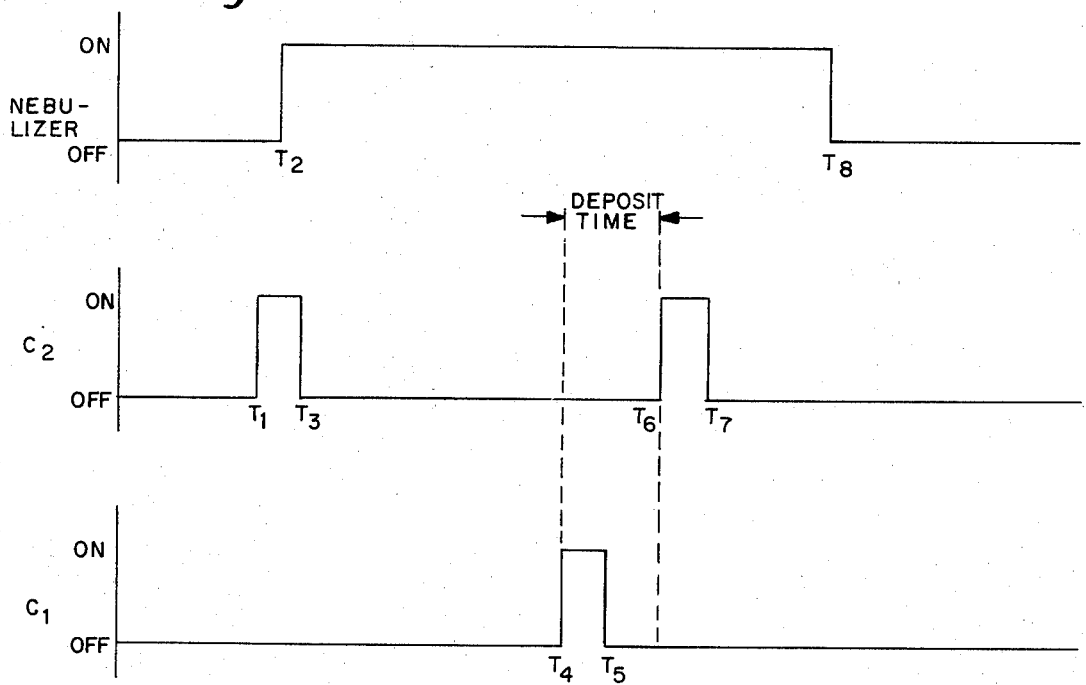
FIG. 11 depicts the timing diagram useful in explaining the operation of this second alternative embodiment of the control means of the invention shown in FIG. 10.

The timing diagram shown in FIG. 11 may best serve to explain the operation of this second embodiment of the control means for effecting deposition of aerosol mist automatically in predetermined and reproducible amounts. As may be noted from this FIG. 11, a control signal is first applied at control port C2 at time T1 for a short period to expire as at T3, during the application of which namely at time T2, a signal is applied to the nebulizer to turn it on. Following the onset of nebulization at T2 and the start of deposition at T4, the only output that is operational through fluidic flip-flop 23 is its Output 2, hence all aerosol mist entering through hose 43 is effectively removed through hose 48 to drain. Deposition is effected by applying a second control signal at the other control port C1, at time T4, which control signal need only last for a short duration, say through T5, so as to switch the output of switch 23 from Output 2 to Output 1. Since Output 1 is represented by delivery nozzle 42a, which is in communication with the introduction aperture 52, deposition of aerosol mist is effected into the furnace atomizer 50. Deposition of aerosol mist will continue until such time that another control signal is applied to control part C2 as at time T6, causing the switching from Output 1 back again to Output 2, which will remain so through time T8, representing the end of the nebulization process, even though this third control signal is sooner terminated as at time T7, i.e., shortly after its application. Consequently, deposition time is precisely controlled by the leading edge of the last two mentioned signals, namely the control signal applied at time T4 at control part C1 and the other signal applied at time T6 at control port C2. This deposition time may be as short as a fraction of a second if so desired or, of course, as long as several seconds if so desired. This fluidic flip-flop 23 may likewise be provided with a burred mounting rod 46a, so as to permit its mounting within the supporting and arcuately guiding means shown in and specifically described with reference to FIGS. 4 and 6 above.

Thus, applicants have shown and described a novel method and apparatus useful for the automatic deposition of predetermined reproducible amounts of aerosol samples, which have been fully equilibrated, into a furnace atomizer of a flameless atomic absorption spectrophotometer in which the deposited amounts of aerosol mist are and can be extremely tightly controlled. Although two specific preferred embodiments have been illustrated and described, it will be obvious to those skilled in the art that various modifications may be made therein without departing from the spirit of the invention, which is intended to be limited solely by the appended claims.

We claim:

1. Apparatus for automatically depositing predetermined reproducible amounts of aerosol samples into a furnace atomizer of an atomic absorption spectrophotometer, with said atomizer being provided with an aperture, comprising a nebulizer-mixing chamber device in communication with a sample container containing sample to be analyzed, means for depositing aerosol samples from said device through said aperture into said furnace atomizer, said means having communication with said device, and means for controlling the amounts of aerosol samples being deposited to assure that the deposited amounts are reproducible comprising a vacuum source in valved communication with said means for depositing aerosol samples whereby aerosol deposition takes place only during the time period when said vacuum source is shut off from said means for depositing by shutting off said valve.

2. Apparatus for automatically depositing predetermined reproducible amounts of aerosol samples into a furnace atomizer of an atomic absorption spectrophotometer, with said atomizer being provided with an aperture, comprising a nebulizer-mixing chamber device in communication with a sample container containing sample to be analyzed, means for depositing aerosol sample from said device through said aperture into said furnace atomizer, said means having communication with said device, and means for controlling the amounts of aerosol samples being deposited to assure that the deposited amounts are reproducible comprising a fluidic switch operatively connected between said device and said means for depositing aerosol samples whereby aerosol deposition takes place only during the time period when said fluidic switch establishes communication from said device to said means for depositing aerosol samples.

3. The apparatus of claim 2 being further characterized in that said fluidic switch is provided with one input port and two output ports and designed to switch on command aerosol samples admitted thereto from one output port to the other, with said input port being connected to said device and one of its said two output ports is connected to said means for depositing aerosol samples.

4. In an apparatus for depositing an aerosol sample to be analyzed into a furnace atomizer of an atomic absorption spectrophotometer, said atomizer having an introduction aperture, the improvement comprising a means for controlling the amount of aerosol sample being deposited through said introduction aperture into said furnace atomizer comprising means defining a delivery passage having a delivery port at the forward end thereof designed to be introduced into said introduction aperture, and an inlet port at its other end designed to be connected to a nebulizer-mixing chamber device operable to produce an aerosol mist, a further port in said delivery passage defining means between said delivery port and said inlet port, and diverting means in communication with said further port for diverting aerosol sample from said delivery port.

5. The apparatus of claim 4 and further including a first mechanism for moving said delivery port between a first position inserted in said introduction aperture and a second position in which said delivery port is remote from said introduction aperture.

6. The apparatus of claim 5 and further including a housing in which said furnace atomizer is mounted, a second mechanism for closing said housing, and means for operating said first and second mechanisms concurrently.

7. Apparatus for depositing an aerosol sample to be analyzed into a furnace atomizer of an atomic absorption spectrophotometer, said atomizer having an aperture, comprising in combination, means for aspirating sample material from a sample container and into a nebulizer-mixing chamber device, means for depositing an aerosol sample from said nebulizer-mixing chamber device through said aperture into said furnace atomizer, said means having communication with said chamber device, and means for controlling the amount of aerosol sample being deposited into said furnace atomizer comprising means defining a delivery passage having a delivery port at the forward end thereof designed to be introduced into said aperture, an inlet port at its other end designed to be connected to said nebulizer-mixing chamber device operable to produce an aerosol mist, and in which said means for controlling the amount of aerosol sample being deposited into said furnace atomizer comprises a further port in said delivery passage defining means between said delivery port and said inlet port, and diverting means in valved communication with said further port for diverting aerosol sample from said delivery port.

8. The apparatus of claim 4 or 7 in which said diverting means include a vacuum source in valved communication with said further port.

9. The apparatus of claim 4 or 7 in which said diverting means includes a fluidic switch having one input port and two output ports and designed to switch on command aerosol mist admitted thereto from one output port to the other, said delivery port connected to one of said output ports of said switch, a tube connected between the second output port of said fluidic switch and waste, and said inlet port connected to said input port of said fluidic switch.

10. Apparatus for depositing an aerosol sample to be analyzed into a furnace atomizer of an atomic absorption spectrophotometer, said atomizer having an aperture, comprising in combination;

means for arranging and successively transporting a plurality of sample containers containing samples to be analyzed on a sample-supporting device, means for aspirating the samples seriatim from said plurality of sample containers and into a nebulizer-mixing chamber device, means for depositing an aerosol sample from said nebulizer-mixing chamber device through said aperture into said furnace atomizer, said means having communication with said chamber device, and means for controlling the amount of aerosol sample being deposited into said furnace atomizer comprising means for diverting aerosol sample from said aperture until aerosol mist equilibrium is achieved.

11. In the apparatus for depositing an aerosol sample of claim 10 in which said diverting means comprises a vacuum source in valved communication with said means for depositing an aerosol sample characterized in that aerosol deposition is effected only during the time period when said vacuum source is shut off from said means for depositing an aerosol sample.

12. The apparatus for depositing an aerosol sample of claim 10 in which said diverting means comprises a fluidic switch operatively connecting said chamber device with said means for depositing an aerosol sample characterized in that aerosol deposition takes place only during the time period when said fluidic switch effectuates such communication from said device to said means for depositing an aerosol sample.

13. The apparatus for depositing an aerosol sample of claim 12 being further characterized in that said fluidic switch is provided with an input port connected to said device and two output ports with one of its output ports being connected to said means for depositing an aerosol sample, said switch designed to switch on command an aerosol sample admitted thereto from one output port to the other.

14. A method of depositing a predetermined reproducible amount of aerosol sample into an analysis cell of an atomic absorption spectrophotometer or the like comprising the steps of nebulizing a sample in a mixing chamber, achieving equilibrium while removing nebulized sample from said chamber, and after equilibrium is achieved, delivering for a set time interval said nebulized sample from said mixing chamber to said analysis cell, permitting thereby a predetermined reproducible amount of said aerosol sample to be delivered from said chamber to said analysis cell.

15. A method of automatically depositing predetermined reproducible amounts of aerosol samples into a furnace atomizer of an atomic absorption spectrophotometer comprising aspirating a sample from a sample container, nebulizing and mixing said sample in a chamber, achieving equilibrium while removing nebulized sample from said chamber, after equilibrium is established, delivering for a set time interval said nebulized sample to said furnace atomizer, permitting thereby the deposition of predetermined reproducible amounts of aerosol samples into said furnace atomizer.

16. Sample apparatus for depositing sample material into an analysis cell of an atomic absorption spectrophotometer or the like comprising:

a nebulizer for nebulizing sample material to be analyzed, transport means for transporting a stream of nebulized sample material between said nebulizer and said analysis cell and having a delivery port for communication with said analysis cell, and control means for controlling the amount of nebulized sample material delivered to said analysis cell, said control means being coupled to said transport means and having a first condition in which a stable flow of nebulized sample through said transport means is established with nebulized sample being diverted from said delivery port, and a second condition in which said stable flow of nebulized sample material from said nebulizer through said transport means is maintained with nebulized sample flowing to said delivery port for delivery to said analysis cell.

17. The apparatus of claim 16 and further including mechanism for moving said delivery port between a first position for delivery of nebulized sample material to said analysis cell and a second position in which said delivery port is remote from said analysis cell.

* * * * *